United States Patent [19]

Yen et al.

[11] 4,203,989
[45] May 20, 1980

[54] ANTI-DIARRHEAL DIARYL-(1-AZABICYCLO(2.2.2)OCTAN-2-YL)-ALKANOLS AND RELATED COMPOUNDS

[75] Inventors: Chung H. Yen, Arlington Hts.; James R. Deason, Wilmette, both of Ill.

[73] Assignee: G. D. Searle & Co., Skokie, Ill.

[21] Appl. No.: 34,889

[22] Filed: Apr. 30, 1979

[51] Int. Cl.$^2$ .................. A61K 31/445; C07D 453/02
[52] U.S. Cl. ...................................... 424/267; 546/133
[58] Field of Search ......................... 546/133; 424/267

[56] References Cited

U.S. PATENT DOCUMENTS

| | | | |
|---|---|---|---|
| 3,917,615 | 11/1975 | Adelstein | 424/267 X |
| 3,998,832 | 12/1976 | Adelstein et al. | 424/267 X |
| 4,013,667 | 3/1977 | Yen | 546/133 |
| 4,017,491 | 4/1977 | Adelstein | 424/267 X |
| 4,086,234 | 4/1978 | Dryden et al. | 260/326.5 D X |
| 4,125,531 | 11/1978 | Yen | 546/133 |

FOREIGN PATENT DOCUMENTS

2502916 9/1975 Fed. Rep. of Germany ........... 546/133

OTHER PUBLICATIONS

Adelstein, G., et al., J. Med. Chem., 19(10), 1221–1225 (1976).

Primary Examiner—Henry R. Jiles
Assistant Examiner—Richard A. Schwartz
Attorney, Agent, or Firm—Michael T. Murphy; Albert Tockman

[57] ABSTRACT

The present invention provides Diaryl-(1-azabicyclo [2.2.2]octan-2-yl)alkanols of the formula

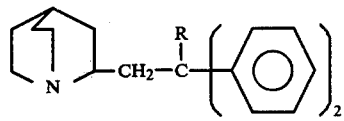

and the pharmaceutically acceptable acid addition salts thereof wherein R is a cycloalkanol having 4–8 carbon atoms, an alkanol having 1–2 carbon atoms, or a radical of the formula

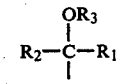

wherein $R_1$ and $R_2$ are each H or a $C_1$–$C_5$ alkyl, and $R_3$ is H or an acyl of the formula

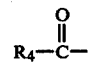

wherein $R_4$ is H or a $C_1$–$C_4$ alkyl.

These alkanols are useful as antidiarrheal agents.

19 Claims, No Drawings

ANTI-DIARRHEAL DIARYL-(1-AZABICYCLO(2.2.2)OCTAN-2-YL)-ALKANOLS AND RELATED COMPOUNDS

DETAILED DESCRIPTION OF THE INVENTION

The present invention encompasses Diaryl-(1-azabicylo [2.2.2]octan-2-yl)alkanols characterized by the formula (I)

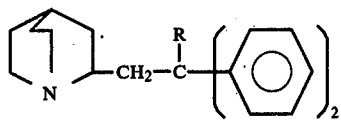

wherein R is a cycloalkanol having 4-8 carbon atoms, an alkanol having 1-2 carbon atoms, or a radical of the formula $$R_2-\underset{\underset{R_1}{|}}{\overset{\overset{OR_3}{|}}{C}}-R_1$$

wherein $R_1$ and $R_2$ are H or a $C_1$-$C_4$ alkyl, and $R_3$ is H or an acyl of the formula

wherein $R_4$ is H or a $C_1$-$C_4$ alkyl.

According to the present invention, in the treatment of diarrhea, an effective anti-diarrheal amount to be administered to an animal ranges from about 0.1 to about 25.0 mg./kg. of a present alkanol.

The term "cycloalkanol" as used herein refers to cycloalkanols having 4-8 carbon atoms such as cyclobutanol, cyclopentanol, cyclohexanol, cyclooctanol and the like.

The compounds of the present invention may be prepared according to the various methods illustrated below in Schemes I, II, III, IV and V.

In both Schemes I and II, in the product compounds (i.e., III and IV, respectively), R is ethanol, i.e. 1-ethanol (Scheme I) and 2-ethanol (Scheme II), where in Scheme III, R is cyclopentanol.

SCHEMES I, II, III:

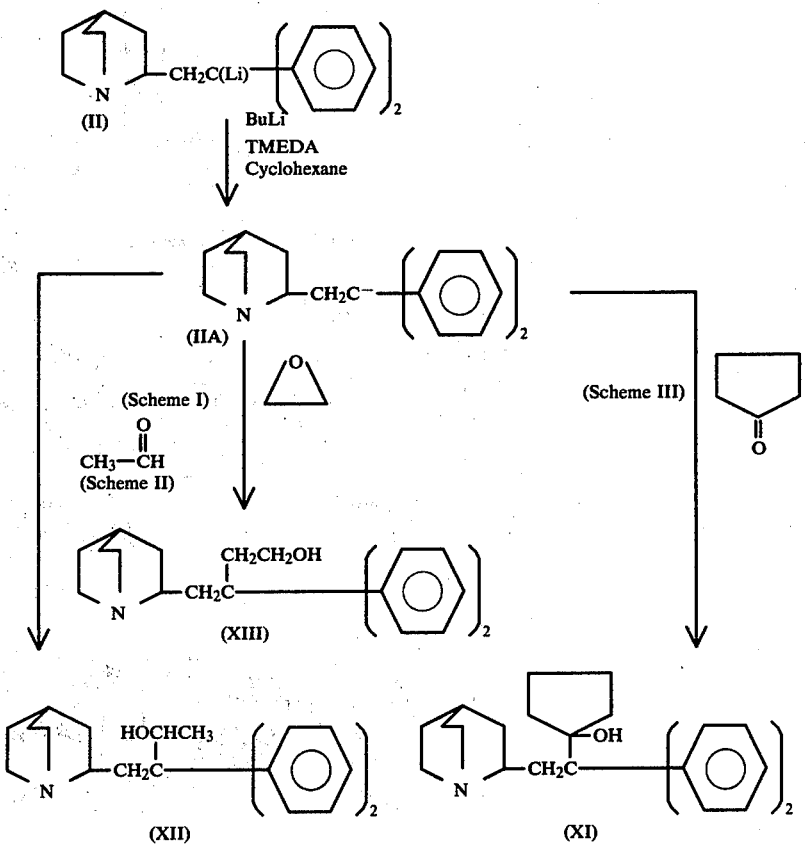

SCHEME I

In this method, 2-(2,2-diphenylethyl)-1-azabicyclo[2.2.2] octane (II) is treated with a solution of butyl lithium and N,N,N',N'-tetramethylethylenediamine in cyclohexane to give an intermediate compound (II A) which is reacted with ethylene oxide and treated to provide the product compound, i.e., gamma, gamma-diphenyl-1-azabicyclo[2.2.2]octane-2-butanol (XIII).

SCHEME II

According to this method, 2-(2,2-diphenylethyl)-1-azabicyclo[2.2.2]octane (II) is treated with a solution of butyl lithium and N,N,N',N'-tetramethylenediamine in cyclohexane to give an intermediate compound (II A) which is reacted with acetaldehyde and treated to provide the product compound, i.e., alpha-methyl-beta,beta-diphenyl-1-azabicyclo[2.2.2]-octane-2-propanol (XII).

SCHEME III

In this method, 2-(2,2-diphenylethyl)-1-azabicyclo[2.2.2]-octane (II) is treated with N,N,N',N'-tetramethylethylenediamine and a solution of butyl lithium in cyclohexane to provide an intermediate compound (II A) which is reacted with cyclopentanone and treated to provide the product compound, i.e., 1-[2-(1-azabicyclo[2.2.2]-octan-2-yl)-1,1-diphenylethyl]cyclopentanol (XI).

In Scheme IV, as illustrated below, in the product compound (VI) R is —CH$_2$OH, and according to Scheme V, as illustrated below, in product compound (X), R is

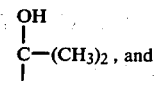

in product compound (IX), R is

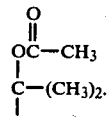

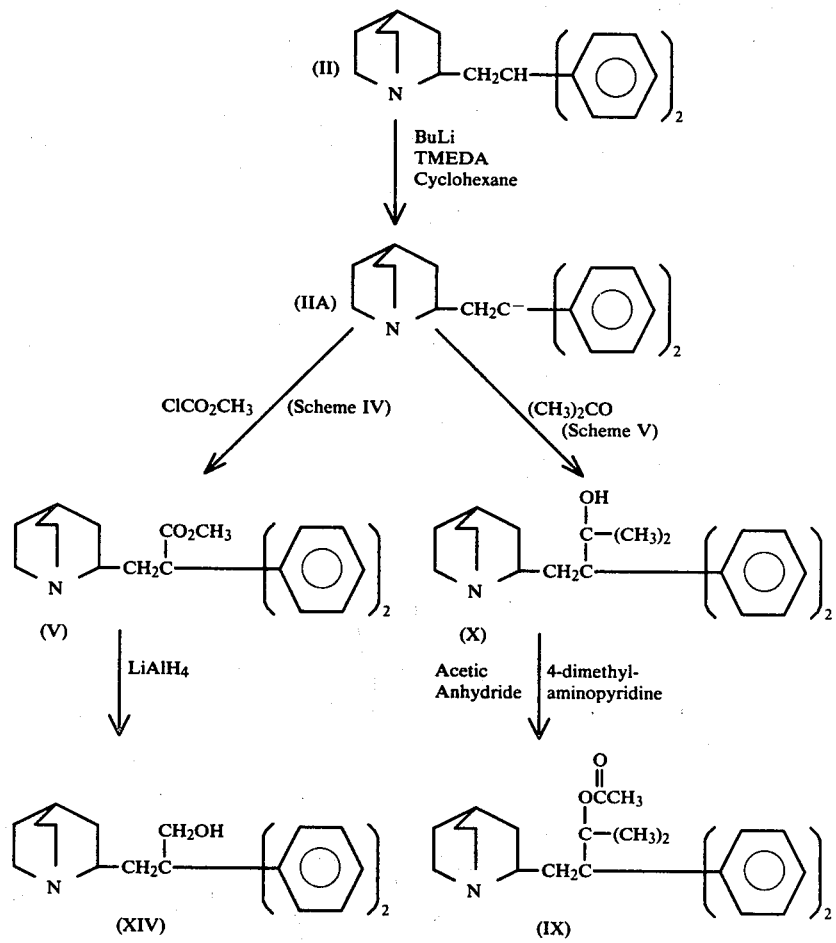

SCHEME IV

In this method, initially 2-(2,2-diphenylethyl)-1-azabicyclo[2.2.2]octane (II) is treated with a solution of butyl lithium and N,N,N',N'-tetramethylethylenediamine in cyclohexane to give an intermediate compound (II A) which is treated with ClCO$_2$CH$_3$ to provide methyl 2,2-diphenyl-3-(1-azabicyclo[2.2.2]-oct-2-yl)propionate (V). The propionate (V) is then mixed with lithium aluminum hydride and treated to provide the product compound, i.e., beta, beta-diphenyl-1-azabicyclo[2.2.2]-octane-2-propanol (XIV).

SCHEME V

According to this method, N,N,N',N'-tetramethylethylenediamine and a solution of butyllithium are added to 2-(2,2-diphenylethyl)-1-azabicyclo[2.2.2]octane in cyclohexane to give an intermediate compound (II A) which is treated with acetone to provide a product compound (VIII), e.g., alpha, alpha-dimethylbeta, beta-diphenyl-1-azabicyclo[2.2.2]octane-2-propanol (X).

Then the solution of the 2-propanol compound (X) is mixed with acetic anhydride and 4-dimethylaminopyridine and treated to yield a product compound (IX), i.e., alpha, alpha-dimethylbeta, beta-diphenyl-1-azabicyclo[2.2.2]octane-2-propanol acetate.

A detailed description of each of the methods summarized above, is set forth below in the Examples.

The compounds produced by the process schemes, illustrated above, and which are preferred embodiments within the scope of the formula (I), include:

Alpha, alpha-dimethyl-beta, beta-diphenyl-1-azabicyclo[2.2.2]octane-2-propanol (X)

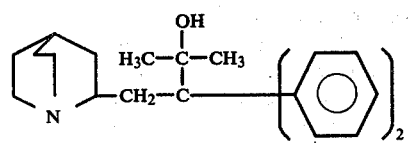

1-[2-(1-azabicyclo[2.2.2]octan-2-yl)-1,1-diphenylethyl]-cyclopentanol (XI)

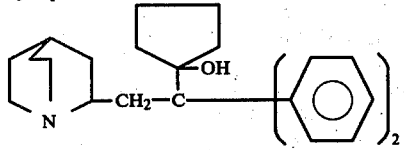

Alpha-methyl-beta, beta-diphenyl-1-azabicyclo[2.2.2]octane-2-propanol (XII)

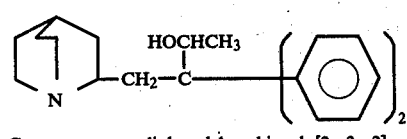

Gamma, gamma-diphenyl-1-azabicyclo[2.2.2]octane-2-butanol (XIII)

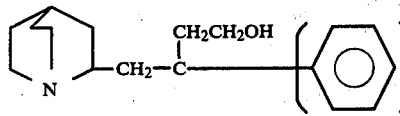

Beta, beta-diphenyl-1-azabicyclo[2.2.2]octane-propanol (XIV)

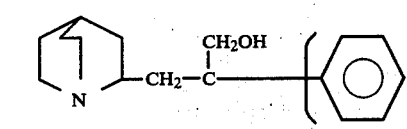

Gamma, gamma-diphenyl-1-azabicyclo[2.2.2]octane-2-butanol hydrochloride (XV)

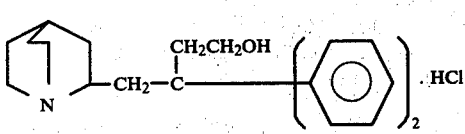

Alpha, alpha-dimethyl-beta, beta-diphenyl-1-azabicyclo[2.2.2]ocatne-2-propanol acetate hydrochloride (XVI)

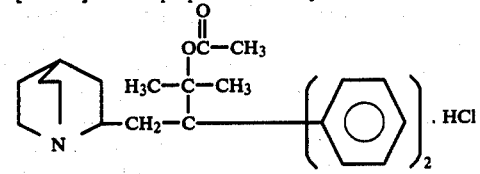

1-[2-(1-azabicyclo[2.2.2]octan-2-yl)-1,1-diphenylethyl]-cyclopentanol hydrochloride (XVII)

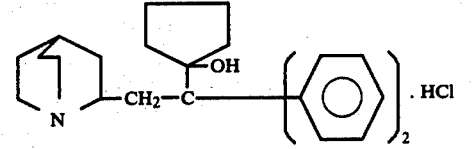

The present compounds are potent anti-diarrheal agents as evidenced by their ability to inhibit gastrointestinal motility as set forth in the following test:

Mouse Cecal Test

The method used for this assay is a modification of the techniques previously described by Macht and Barb-Gose, J. Amer. Pharm. Ass., 20, 558 (1931), and Janssen and Jageneau, J. Pharm. Pharmacol., 9, 381 (1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

| Compound | $ED_{50} \pm$ S.E. mg./kg. IG |
|---|---|
| alpha, alpha-dimethyl-beta, beta-diphenyl-1-azabicyclo[2.2.2]-octane-2-propanol | 1.60 ± 0.28 |
| 1-[2-(1-azabicyclo[2.2.2]octan-2-yl)-1,1-diphenylethyl]cyclopentanol | 7.61 ± 2.23 |
| gamma, gamma-diphenyl-1-azabicyclo[2.2.2]octane-2-butanol | 6.39 ± 2.09 |
| gamma, gamma-diphenyl-1-azabicyclo[2.2.2]octane-2-butanol hydrochloride | 1.20 ± 0.25 |
| 1-[2-(1-azabicyclo[2.2.2]octan-2-yl)-1,1-diphenylethyl]cyclopentanol hydrochloride | 1.78 ± 0.83 |

The compounds herein described can be combined with pharmaceutically acceptable carriers to provide novel pharmaceutical compositions. The concentration of active ingredient in the composition is not critical, but is preferably 1–80%. These compositions can be administered orally, suitable forms for each administration including tablets, lozenges, capsules, degrees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin, talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as peanut oil, cottonseed oil, sesame oil; olive oil, corn oil, oil of theobroma; water, agar; alginic acid; and benzyl alcohol, as well as other non-toxic compatible substances used in pharmaceutical formulations.

The compounds of this invention can be used to produce an anti-diarrheal effect in mammals by administering the instant novel compositions containing a therapeutically effective amount of the active ingredient. The term "therapeutically effective amount" is defined as the amount of active ingredient that will produce an anti-diarrheal effect, i.e., which will reverse, inhibit or prevent diarrhea. For a particular subject, the amount of active ingredient to be used will vary with the subject involved, the severity of the diarrhea, and the particular active ingredient used. The therapeutically effective amount of a particular active ingredient can be determined by comparing its potency to that of a known standard, for which the therapeutic dosage is known. Typically 0.1–25 mg/kg is an effective anti-diarrheal amount of a given compound.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade (° C.).

EXAMPLE 1

Alpha, alpha-dimethyl-beta, beta-diphenyl-1-azabicyclo[2.2.2]octane-2-propanol (X)

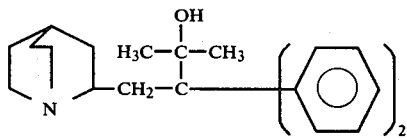

15 parts by volume of N,N,N',N'-tetramethylethylenediamine and 69 parts by volume of a 1.6 M solution of butyllithium in hexane are added to a solution of 29.1 parts 2-(2,2-diphenylethyl)-1-azabicyclo[2.2.2]octane in 600 parts by volume of cyclohexane under nitrogen. The resultant solution is heated at reflux while being stirred for 1 hour and then cooled to 10° resulting in an orange-red mixture containing a solid. 8.8 parts by volume of acetone (reagent grade) is added at 10° to 15° during a period of 10 minutes at the end of which the orange-red color has disappeared. The reaction mixture is washed three times with water, dried over anhydrous sodium sulfate and evaporated under vacuum giving a residue of a solid and oil. This residue is put on a 25 mm column of Woelm silica gel and eluted with a mixed solvent of ethanol, concentrated ammonia and toluene (ratio 4:0.25:96 by volume) under a pressure to maintain a flow rate of 8 ml. per minute. The desired eluate was collected and evaporated under reduced pressure. The residual gum obtained is crystallized from n-pentane and gives the product as colorless prisms: (X) alpha, alpha-dimethyl-beta, beta-diphenyl-1-azabicyclo[2.2.2]octane-2-propanol; m.p. 159°–160.5°; MW 350.

EXAMPLE 2

1-[2-(1-azabicyclo[2.2.2]octan-2-yl)-1,1-diphenylethyl] cyclopentanol (XI)

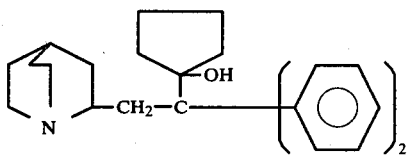

A solution of 20.4 parts 2-(2,2-diphenylethyl)-1-azabicyclo[2.2.2]octane, 10.5 parts by volume of N,N,N',N'-tetramethylethylenediamine, 48 parts by volume of a 1.6 M solution of butyllithium in hexane in 500 parts by volume of cyclohexane is heated to reflux while being stirred for 1.2 hours under nitrogen. The reaction mixture is cooled to 10 and 6.8 parts by volume of cyclopentanone is added during 5 minutes. It is washed four times with water and one time with saturated sodium chloride solution, dried over anhydrous sodium sulfate and evaporated under reduced pressure. The residual solid is triturated with 40 parts diethyl ether and filtered. The filtrate is evaporated under reduced pressure to give residual solid and oil. This residue is put on a 25 mm volume of Woelm silica gel and eluted with a mixed solvent of ethanol, concentrated ammonia and toluene (ratio 2:0.25:98) under a pressure to maintain a flow rate of 8 ml per minute. The desired fraction is evaporated under reduced pressure giving residual oil which solidifies. The solid is washed with n-pentane and recrystallized from diethylether giving the product as a white solid: (XI) 1-[2-(1-azabicyclo [2.2.2]octan-2-yl)-1,1-diphenylethyl]cyclopentanol m.p. 178°–179.5°, MW 376. The hydrochloride of this compound is crystallized from a mixed solvent of isopropanol and diethyl ether: 1-[2-(1-azabicyclo[2.2.2]octan-2-yl)-1,1-diphenylethyl] cyclopentanol hydrochloride (XVII); m.p. 247°–249°; MW 412.

EXAMPLE 3

Gamma, gamma-diphenyl-1-azabicyclo[2.2.2]octane-2-butanol (XIII)

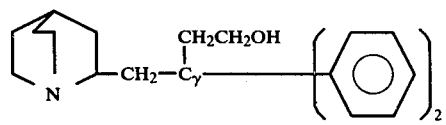

A solution of 10.0 parts 2-(2,2-diphenylethyl)-1-azabicyclo [2.2.2]octane, 25.6 parts by volume of a 1.6 M solution of butyllithium in hexane and 5.16 parts by volume N,N,N',N'-tetramethylethylenediamine in 400 parts by volume cyclohexane is heated to reflux while being stirred for 1.25 hours under nitrogen and then cooled to 10°. 8.3 parts ethylene oxide in 100 parts by volume cyclohexane is added during a period of 30 minutes. The reaction mixture is washed with water and extracted with dilute HCl. The acidic aqueous extract is washed with ether-cyclohexane (1:1), made strongly alkaline with aqueous sodium hydroxide and extracted with ether. The ethereal extract is dried with Na₂SO₄ and evaporated to a small volume which is diluted with n-pentane to effect crystallization. The crystals are collected and recrystallized from Skellysolve B yielding the product: gamma, gamma-diphenyl-1-azabicyclo[2.2.2]octane-2-butanol (XIII); m.p. 122°-124°; MW 335.

The hydrochloride of this compound is crystallized from acetone-ether: gamma, gamma-diphenyl-1-azabicyclo[2.2.2]octane-2-butanol hydrochloride (XV); m.p. 234°-236°; MW 372.

EXAMPLE 4

Beta, beta-diphenyl-1-azabicyclo[2.2.2]octane-2-propanol (XIV)

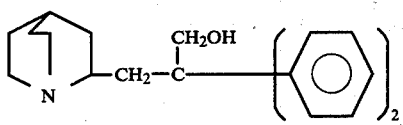

A solution of 2.0 parts methyl 2,2-diphenyl-3-(1-azabicyclo[2.2.2]-oct-2-yl)propionate in 80 parts by volume of dry ether is added with stirring to a suspension of 0.55 parts of lithium aluminum hydride under nitrogen. The reaction mixture is heated to reflux while being stirred under nitrogen for 2.5 hours and then allowed to stand at room temperature for 17 hours. The mixture is decomposed with 0.58 parts by volume of water, 0.44 parts by volume of 20% NaOH and 2.0 parts by volume of water and filtered. The filtrate is evaporated under reduced pressure giving a residual solid. This solid is recrystallized from diethyl ether-n-pentane and then again from Skellysolve B yielding the product: beta, beta-diphenyl-1-azabicyclo[2.2.2]octane-2propanol(XIV); m.p. 125.5°-127°; MW 321.

EXAMPLE 5

Alpha, alpha-dimethyl-beta, beta-diphenyl-1-azabicyclo[2.2.2]octane-2-propanol acetate hydrochloride (XVI)

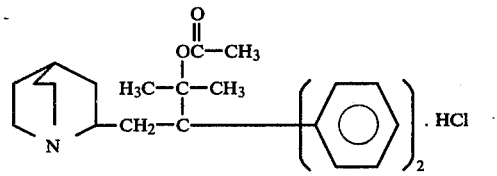

A solution of 0.5 parts alpha, alpha-dimethyl-beta, beta-diphenyl-1-azabicyclo[2.2.2]octane-2-propanol, 2 parts by volume of acetic anhydride and 0.005 parts 4-dimethylaminopyridine in 50 parts by volume dry ether is allowed to stand for 10 days. Reaction mixture is partitioned between ether and dilute NaOH. The ethereal layer is separated, washed with water, dried over Na₂SO₄ and evaporated under reduced pressure. The residual gum, 2.0 parts by volume of acetic anhydride and 0.020 parts of 4-dimethylaminopyridine are mixed. The resulting solution is allowed to stand for 41 hours and poured into dilute NaOH. After subsequent extraction with ether, the ethereal extract is extracted with dilute HCl. The acidic aqueous extract is made strongly alkaline with aqueous NaOH and extracted with ether. The ethereal extract is washed with water, dried over Na₂SO₄ and evaporated under reduced pressure. The residual gum is dissolved in dry ether and then treated with a slight excess of 7N HCl in isopropanol resulting in a gummy precipitate. The combined ethereal layer and the gummy precipitate are evaporated under reduced pressure. The residual gum is then crystallized from methanol-ether and then from acetone yielding the product: alpha, alpha-dimethyl-beta, beta-diphenyl-1-azabicyclo[2.2.2]octane-2-propanol acetate hydrochloride (XVI); m.p. 229°-230°; MW 428.

EXAMPLE 6

Alpha-methyl-beta, beta-diphenyl-1-azabicyclo[2.2.2]octane-2-propanol (XII)

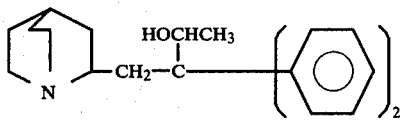

A solution of 10.0 parts 2-(2,2-diphenylethyl)-1-azabicyclo[2.2.2]-octane, 24.7 parts by volume of a 1.6 M solution of butyllithium in hexane and 2.8 parts by volume of N, N,N',N'-tetramethylethylenediamine in 200 parts by volume of cyclohexane is heated to reflux with stirring under nitrogen for 1.5 hours. The resulting red solution is cooled in an ice-ethanol bath. 100 parts by volume of dry tetrahydrofuran is then added when the temperature reaches 10°. Finally, 2.23 parts by volume of tetrahydrofuran in 40 parts by volume of cyclohexane is added dropwise and with stirring at −5° to 0°. The reaction mixture is allowed to warm to room temperature, then washed with water and extracted with dilute HCl. The dilute HCl extract is made strongly alkaline with aqueous NaOH and extracted with ether. The ethereal extract is dried over Na₂SO₄ and evaporated under reduced pressure. The residue is triturated with 20 parts by volume of ether. The undissolved solid is filtered off, washed with ether and recrystallized from diethyl ether-n-pentane giving alpha-methyl-beta, beta-diphenyl-1-azabicyclo [2.2.2]octane-2-propanol (XII); m.p. 175°-177°; MW 335.

We claim:

1. A compound of the formula

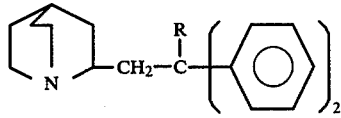

or a pharmaceutically acceptable acid addition salt thereof wherein R is a cycloalkanol having 4–8 carbon atoms, an alkanol having 1–2 carbon atoms, or a radical of the formula

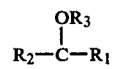

wherein $R_1$ and $R_2$ are each H or a $C_1$–$C_5$ alkyl, and $R_3$ is H or an acyl of the formula $$R_4-\overset{O}{\underset{\|}{C}}-$$

wherein $R_4$ is H or a $C_1$–$C_4$ alkyl.

2. A compound according to claim 1 which is 1-[2-(1-azabicyclo[2.2.2]octan-2-yl)-,1-diphenylethyl]cyclopentanol.

3. A compound according to claim 1 which is 1-[2-(1-azabicyclo[2.2.2]octan-2-yl)-1,1-diphenylethyl]cyclopentanol hydrochloride.

4. A compound according to claim 1 which is gamma, gamma-diphenyl-1-azabicyclo[2.2.2]octane-2-butanol.

5. A compound according to claim 1 which is gamma, gamma-diphenyl-1-azabicyclo[2.2.2]octane-2-butanol hydrochloride.

6. A compound according to claim 1 which is alpha-methyl-beta, beta-diphenyl-1-azabicyclo[2.2.2]octane-2-propanol.

7. A compound according to claim 1 which is alpha, alpha-dimethyl-beta, beta-diphenyl-1-azabicyclo[2.2.2]octane-2-propanol.

8. A compound according to claim 1 which is beta, beta-diphenyl-1-azabicyclo[2.2.2]octane-2-propanol.

9. A compound according to claim 1 which is alpha, alpha-dimethyl-beta, beta-diphenyl-1-azabicyclo[2.2.2]octane-2-propanol acetate hydrochloride.

10. A method of treating diarrhea comprising administering to an animal in need of anti-diarrheal treatment an effective anti-diarrheal amount of a compound of the formula

[structural formula]

or a pharmaceutically acceptable acid addition salt thereof wherein R is a cycloalkanol having 4–8 carbon atoms, an alkanol having 1–2 carbon atoms, or a radical of the formula $$R_2-\overset{OR_3}{\underset{|}{\underset{|}{C}}}-R_1$$

wherein $R_1$ and $R_2$ are each H or a $C_1$–$C_5$ alkyl, and $R_3$ is H or an acyl of the formula $$R_4-\overset{O}{\underset{\|}{C}}-$$

wherein $R_4$ is H or a $C_1$–$C_4$ alkyl.

11. A method according to claim 10, wherein the effective anti-diarrheal amount of said compound ranges from about 0.1 to about 25.0 mg/kg.

12. A method according to claim 10, wherein the compound is 1-[2-(1-azabicyclo[2.2.2]octan-2-yl)-1,1-diphenylethyl]cyclopentanol.

13. A method according to claim 10, wherein the compound is 1-[2-(1-azabicyclo[2.2.2]octan-2-yl)-1,1-diphenylethyl]cyclopentanol, hydrochloride.

14. A method according to claim 10, wherein the compound is gamma, gamma-diphenyl-1-azabicyclo[2.2.2]octane-2-butanol.

15. A method according to claim 10, wherein the compound is gamma, gamma-diphenyl-1-azabicyclo[2.2.2]octane-2-butanol hydrochloride.

16. A method according to claim 10, wherein the compound is alpha-methyl-beta, beta-diphenyl-1-azabicyclo[2.2.2]octane-2-propanol.

17. A method according to claim 10, wherein the compound is alpha, alpha-dimethyl-beta, beta-diphenyl-1-azabicyclo[2.2.2]octane-2-propanol.

18. A method according to claim 10, wherein the compound is beta, beta-diphenyl-1-azabicyclo[2.2.2]octane-2-propanol.

19. A method according to claim 10, wherein the compound is alpha, alpha-dimethyl-beta, beta-diphenyl-1-azabicyclo[2.2.2]octane-2-propanol acetate hydrochloride.

* * * * *